United States Patent

Flockerzi et al.

[11] Patent Number: 4,707,486
[45] Date of Patent: Nov. 17, 1987

[54] DIARYL PIPERIDINE CONTAINING ESTERS OF 1,4-DIHYDROPYRIDINES AND CORONARY THERAPEUTIC USE

[75] Inventors: Dieter Flockerzi; Kurt Klemm, both of Allensbach; Wolf-Rudiger Ulrich, Constance, all of Fed. Rep. of Germany

[73] Assignee: Byk Gulden Lomberg Chemische Fabrik GmbH, Constance, Fed. Rep. of Germany

[21] Appl. No.: 781,808

[22] Filed: Sep. 30, 1985

[30] Foreign Application Priority Data

Sep. 28, 1984 [CH] Switzerland ............ 4653/84
Sep. 28, 1984 [CH] Switzerland ............ 4652/84

[51] Int. Cl.$^4$ ............... A61K 31/455; C07D 401/12; C07D 413/14
[52] U.S. Cl. ................................. 514/318; 546/193; 546/194
[58] Field of Search ............. 546/193, 194; 514/318

[56] References Cited

U.S. PATENT DOCUMENTS 4,532,248 7/1985 Franckowink et al. ............ 514/237

FOREIGN PATENT DOCUMENTS 0088903 9/1983 European Pat. Off. ............ 546/194
0094159 11/1983 European Pat. Off. ............ 544/364
0106276 4/1984 European Pat. Off. ............ 546/194

OTHER PUBLICATIONS

Burger, A., Medicinal Chemistry, second edition, 1960, Interscience Publishers, New York, pp. 566, 568, 580, 600, 601.
Thomas, G. et al., Journal of Cardiovascular Pharmacy, 6:1170–1176, 1984.

Primary Examiner—Richard A. Schwartz
Assistant Examiner—Dale A. Bjorkman
Attorney, Agent, or Firm—Berman, Aisenberg & Platt

[57] ABSTRACT

Diaryl compounds of formula I

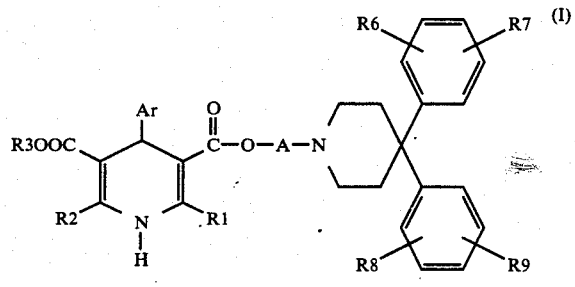

wherein Ar represents a ring of the formula

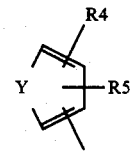

in which Y denotes oxygen (O), sulfur (S), vinylene (—CH=CH—), azomethine (—CH=N—) or a group of the formula

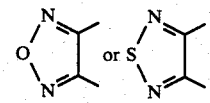

R1, R2 and R3 are identical or different and denote hydrogen, $C_1$–$C_6$-alkyl, $C_3$–$C_7$-alkoxyalkyl, aryl, aryl-$C_1$–$C_6$-alkyl or aryloxy-$C_1$–$C_6$-alkyl,
R4 and R5 are identical or different and denote hydrogen, hydroxyl, halogen, nitro, cyano, trifluoromethyl, $C_1$–$C_4$-alkyl, $C_1$–$C_4$-alkoxy, $C_1$–$C_4$-alkoxy which is completely or partly substituted by fluorine, $C_1$–$C_4$-alkoxycarbonyl, $C_2$–$C_5$-acyl, amino or mono- or di-$C_1$–$C_4$-alkylamino,
R6, R7, R8 and R9 are identical or different and denote hydrogen, hydroxyl, halogen, $C_1$–$C_4$-alkyl, $C_1$–$C_4$-alkoxy, amino, mono- or di-$C_1$–$C_4$-alkylamino, or $C_1$–$C_4$-alkoxy which is completely or partly substituted by fluorine, and
A denotes straight-chain or branched $C_2$–$C_5$-alkylene, which can be substituted by $C_1$–$C_4$-alkoxy or aryl,
and their salts are new compounds for the treatment and prophylaxis of diseases of circulatory origin.

18 Claims, No Drawings

DIARYL PIPERIDINE CONTAINING ESTERS OF 1,4-DIHYDROPYRIDINES AND CORONARY THERAPEUTIC USE

FIELD OF THE INVENTION

The invention relates to new diaryl compounds, processes for their preparation, their use and medicaments containing them. The compounds according to the invention are employed in the pharmaceutical industry for the preparation of medicaments and for the treatment and propylaxis of diseases of circulatory origin.

TECHNICAL BACKGROUND

Certain 1,3-dihydropyridine derivatives (substituted in various ways) have pharmacologically-useful properties. European Patent Application Nos. 88,903, 94,159, and 106,276 provide examples. Surprisingly, it has now been found that new compounds (hereinafter described in more detail) which, in contrast to prior art compounds, carry a piperidine ring (which is disubstituted in the 4-position) have particularly interesting pharmacological properties by which they differ advantageously from their noted prior art counterparts.

SUMMARY OF THE INVENTION

The invention relates to new diaryl compounds of formula I

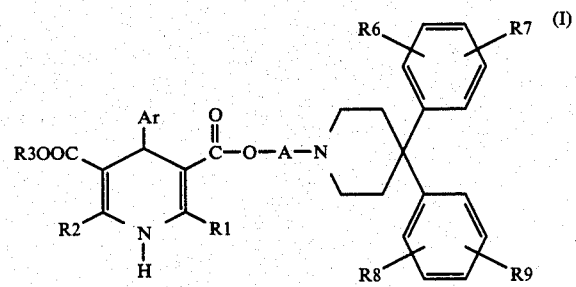

wherein
Ar represents a ring of the formula

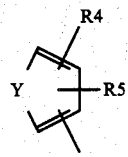

in which Y denotes oxygen (O), sulfur (S), vinylene (—CH=CH—), azomethine (—CH=N—) or a group of the formula

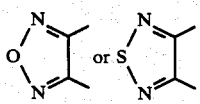

$R_1$, $R_2$ and $R_3$ are identical or different and denote hydrogen (—H), $C_1$–$C_6$-alkyl, $C_3$–$C_7$-alkoxyalkyl, aryl, aryl-$C_1$–$C_6$-alkyl or aryloxy-$C_1$–$C_6$-alkyl,
$R_4$ and $R_5$ are identical or different and denote hydrogen (—H), hydroxyl (—OH), halo, nitro, cyano, trifluoromethyl, $C_1$–$C_4$alkyl, $C_1$–$C_4$-alkoxy, $C_1$–$C_4$-alkoxy which is completely or partly substituted by fluorine, $C_1$–$C_4$-alkoxycarbonyl, $C_2$–$C_5$-acyl (alkylcarbonyl), amino or mono- or di-$C_1$–$C_4$-alkylamino.,
$R_6$, $R_7$, $R_8$ and $R_9$ are identical or different and denote hydrogen (—H), hydroxyl (—OH), halo, $C_1$–$C_4$-alkyl, $C_1$–$C_4$-alkoxy, amino, mono- or di-$C_1$–$C_4$-alkylamino, or $C_1$–$C_4$-alkoxy which is completely or partly substituted by fluorine, and
A denotes straight-chain or branched $C_2$–$C_5$-alkylene, which is optionally substituted by $C_1$–$C_4$-alkoxy or aryl;
and their salts.

In addition to the noted compounds and their salts, this invention has a number of distinct aspects, which are not limited to but include:
(a) synthesis of the compounds and their salts,
(b) converting free bases to acid-additional salts, and converting acid addition salts to free bases or to other acid-addition salts,
(c) converting salts which are not pharmacologically acceptable to those which are,
(d) medicament compositions based on the subject compounds and/or their salts, such compositions optionally containing one or more other compatible pharmacologically-active components,
(e) using the compositions, the compounds and/or their salts for treatment or prophylaxis of hypertension, coronary heart disease, disturbance in peripheral and cerebral circulation and/or disease based on an increased retention of water or sodium, and
(f) novel intermediates in the synthesis of the compounds.

DETAILS

The terms (other than "salts") used to identify substituents of formula I are restricted to those which do not render the resulting compounds pharmacologically unacceptable. Such terms are otherwise unlimited. Exemplification follows:

$C_1$–$C_6$-Alkyl is straight-chain or branched and denotes, for example, a hexyl, neopentyl, isopentyl, butyl, i-butyl, sec.-butyl, t-butyl, propyl, isopropyl or, in particular, ethyl or methyl radical.

$C_3$–$C_7$-Alkoxyalkyl represents, for example, a methoxyethyl, ethoxyethyl, propoxyethyl, isopropoxyethyl, butoxyethyl, methoxypropyl, 2-methoxy-1-methylethyl or 2-ethoxy-1-methylethyl radical.

Aryl generally represents phenyl or substituted phenyl with one or two substituents from the group comprising halogen, hydroxyl, nitro, cyano, trifluoromethyl, $C_1$–$C_4$-alkoxy, $C_1$–$C_4$-alkoxycarbonyl, $C_2$–$C_5$-acyl (alkylcarbonyl), amino and mono- or di-$C_1$–$C_4$-alkylamino. The only limitation on the aryl is that it must be one which does not negate the pharmacological acceptability of the resulting compound of formula I.

Aryl-$C_1$–$C_6$-alkyl is $C_1$–$C_6$-alkyl which is substituted by aryl. Aryl-$C_1$–$C_6$-alkyl is, for example, phenethyl, 3-(4-chlorophenyl)-propyl or, in particular, benzyl.

Aryloxy-$C_1$–$C_6$-alkyl is $C_1$–$C_6$-alkyl which is substituted by aryloxy. Aryloxy-$C_1$–$C_6$-alkyl is, for example, phenoxyethyl.

Halogen or halo denotes, e.g., bromine and, in particular, fluorine and chlorine.

$C_1$–$C_4$-Alkyl is straight-chain or branched and denotes, for example, a butyl, i-butyl, sec.-butyl, t-butyl, propyl, isopropyl, ethyl or, in particular, methyl radical.

In addition to the oxygen atom, $C_1$–$C_4$-alkoxy contains one of the noted $C_1$–$C_4$-alkyl radicals. The methoxy radical is preferred.

$C_1-C_4$-Alkoxy which is completely or partly substituted by fluorine is, for example, 1,1,2,2-tetrafluoroethoxy, trifluoromethoxy, 2,2,2-trifluoroethoxy or difluoromethoxy.

In addition to the carbonyl group, $C_1-C_4$-alkoxycarbonyl contains one of the noted $C_1-C_4$-alkoxy radicals. The methoxycarbonyl and ethoxycarbonyl radical are preferred.

In addition to the carbonyl group, $C_2-C_5$-acyl contains one of the noted $C_1-C_4$-alkyl radicals. The acetyl radical is the preferred alkylcarbonyl.

In addition to the nitrogen atom, mono- or di-$C_1-C_4$-alkylamino contains one or two of the noted $C_1-C_4$-alkyl radicals. Di-$C_1-C_4$-alkylamino is preferred, and especially dimethyl-, diethyl- or diisopropyl-amino.

Straight-chain or branched $C_2-C_5$-alkylene is, for example, tetramethylene, 1,2-dimethylethylene, 1,1-dimethylethylene, 2,2-dimethylethylene, isopropylidene, 1-methylethylene, 2-ethylpropylene or, in particular, ethylene or propylene.

$C_2-C_5$-Alkylene which is substituted by $C_1-C_4$-alkoxy is, for example, 1-methoxy-propylene, 2-ethoxy-propylene or 1,2-dimethoxyethylene.

$C_2-C_5$-Alkylene which is substituted by aryl is, for example, 1-phenylethylene or 2-(4-chlorophenyl)-propylene.

The salts include all salts with acids. The pharmacologically-acceptable salts of inorganic and organic acids usually employed in the pharmaceutical industry are particularly noteworthy. Pharmacologically-unacceptable salts (which are obtained, for example, as process products when the compounds according to the invention are prepared on an industrial scale) are converted into pharmacologically-acceptable salts by conventional processes which are known to the expert. Examples of suitable salts are water-soluble and water-insoluble acid-addition salts, such as the hydrochloride, hydrobromide, hydriodide, phosphate, nitrate, sulfate, acetate, citrate, gluconate, benzoate, hibenzate, fendizoate, butyrate, sulfosalicylate, maleate, laurate, malate, fumarate, succinate, oxalate, tartrate, amsonate, embonate, metembonate, stearate, tosylate, 2-hydroxy-3-naphthoate, 3-hydroxy-2-naphthoate or mesylate, and also salts with bumethanide, furosemide, azosemide, galosemide, besunide, piretanide, etacrynic acid, tienilic acid or 4-chloro-sulfamoyl-benzoic acid.

Radicals Ar which are noteworthy are the phenyl, 3-fluorophenyl, 2-chlorophenyl, 3-chlorophenyl, 4-chlorophenyl, 2,3-dichlorophenyl, 2-cyanophenyl, 3-cyanophenyl, 2-methoxyphenyl, 3-methoxyphenyl, 2-trifluoromethylphenyl, 3-trifluoromethylphenyl, 3-(1,1,2,2-tetrafluoroethoxy)-phenyl, 2difluoromethoxyphenyl, 3-difluoromethoxyphenyl, 2-tolyl, 3-tolyl, 4-tolyl, 2-pyridyl, 3-pyridyl, 2,1,3-benzoxadiazol-4-yl, 5-methyl-2-thienyl and, in particular, 2-nitrophenyl and 3-nitrophenyl radical.

Embodiments of the invention and preferred and particularly preferred embodiments are given in the claims.

Examples of compounds according to the invention are:

3-ethyl 5-[2-(4,4-diphenylpiperid-1-yl)-ethyl] 1,4-dihydro-2,6-dimethyl-4-(3-nitrophenyl)-piperidine-3,5-dicarboxylate, 3-(2-methoxyethyl) 5-[3-(4,4-diphenylpiperid-1-yl)-propyl]1,4-dihydro-2,6-dimethyl-4-(3-nitrophenyl)-pyridine-3,5-dicarboxylate, 3-methyl 5-[4-(4,4-diphenylpiperid-1-yl)-butyl] 1,4-dihydro-2,6-dimethyl-4-(3-nitrophenyl)-pyridine-3,5-dicarboxylate, 3-methyl 5-[2-(4,4-diphenylpiperid-1-yl)-ethyl] 1,4-dihydro-2,6-dimethyl-4-(2-nitrophenyl)-pyridine-3,5-dicarboxylate, 3-methyl 5-[2-(4,4-diphenylpiperid-1-yl)-ethyl] 1,4-dihydro-2,6-diethyl-4-(3-nitrophenyl)-pyridine-3,5-dicarboxylate, 3-(prop-2-yl) 5-[-(4,4-diphenylpiperid-1-yl)-ethyl] 1,4-dihydro-2,6-dimethyl-4-(3-nitrophenyl)-pyridine-3,5-dicarboxylate, 3-hexyl 5-[2-(4,4-diphenylpiperid-1-yl)-ethyl] 1,4-dihydro-2,6-dimethyl-4-(3-nitrophenyl)-pyridin-3,5-dicarboxylate, 3-(2-n-butoxyethyl) 5-[2-(4,4-diphenylpiperid-1-yl)-ethyl] 1,4-dihydro-2,6-dimethyl-4-3-nitrophenyl)-pyridine-3,5-dicarboxylate, 3-methyl 5-{2-[4,4-di(4-methoxyphenyl)-piperid-1-yl]-ethyl} 1,4-dihydro-2,6-dimethyl-4-(3-nitrophenyl)-pyridine-3,5-dicarboxylate, 3-ethyl 5-[2-(4,4-diphenylpiperid-1-yl)-ethyl] 1,4-dihydro-2,6-dimethyl-4-(2-trifluoromethylphenyl)-pyridine-3,5-dicarboxylate, 3-methyl 5-[2-(4,4-diphenylpiperid-1-yl)-ethyl] 1,4-dihydro-2,6-dimethyl-4-[3-(1,1,2,2-tetrafluoroethoxyl)-phenyl]pyridine-3,5-dicarboxylate, 3-ethyl 5-[2-(4,4-diphenylpiperid-1-yl)-ethyl] 1,4-dihydro-2,6-dimethyl-4-(2-difluoromethoxyphenyl)-pyridine-3,5-dicarboxylate, 3-ethyl 5-[4-(4,4-diphenylpiperid-1-yl)-butyl] 1,4-dihydro-2,6-dimethyl-4-(2-difluoromethoxyphenyl)-pyridine-3,5-dicarboxylate, 3-methyl 5-[2-(4,4-dihydroxyphenylpiperid-1-yl)-ethyl] 1,4 dihydro-2,6-dimethyl-4-(3-nitrophenyl)-pyridine-3,5-dicarboxylate, 3-methyl 5-[2-(4,4-diphenylpiperid-1-yl)-ethyl] 4-(2,3-dichlorophenyl)-1,4-dihydro-2,6-dimethylpyridine-3,5-dicarboxylate, 3-methyl 5-[2-(4,4-diphenylpiperid-1-yl)-ethyl] 4-(2,1,3-benzoxadiazol-4-yl)-1,4-dihydro-2,6-dimethylpyridine-3,5-dicarboxylate, 3-methyl 5-[2-(4,4-diphenylpiperid-1-yl)-ethyl] 4-(3-cyanophenyl)-1,4-dihydro-2,6-dimethylpyridine-3,5-dicarboxylate, 3-methyl 5-[2-(4,4-diphenylpiperid-1-yl)-ethyl] 1,4-dihydro-2,6-dimethyl-4-(2-methoxyphenyl)-pyridine-3,5-dicarboxylate, 3-methyl 5-[2-(4,4-diphenylpiperid-1-yl)-ethyl] 1,4-dihydro-2,6-dimethyl-4-(2-pyridyl)-pyridine-3,5-dicarboxylate, 3-methyl 5-[2-(4,4-diphenylpiperid-1-yl)-ethyl] 1,4-dihydro-2,6-dimethyl-4-(5-methyl-2-thienyl)-pyridine-3,5-dicarboxylate, 3-methyl 5-{2-[4-(4-chlorophenyl)-4-phenylpiperid-1-yl]ethyl} 1,4-dihydro-2,6-dimethyl-4-(3-nitrophenyl)-pyridine-3,5-dicarboxylate, 3-methyl 5-[3-(4,4-diphenylpiperid-1-yl)-propyl] 1,4-dihydro-2,6-dimethyl-4-(2-nitrophenyl)-pyridine-3,5-dicarboxylate, 3-methyl 5-[3-(4,4-diphenylpiperid-1-yl)-propyl] 1,4-dihydro-2,6-diethyl-4-(3-nitrophenyl)-pyridine-3,5-dicarboxylate, 3-(prop-2-yl) 5-[3-(4,4-diphenylpiperid-1-yl)-propyl] 1,4-dihydro-2,6-dimethyl-4-(3-nitrophenyl)-pyridine-3,5-dicarboxylate, 3-hexyl 5-[3-(4,4-diphenylpiperid-1-yl)-propyl] 1,4-dihydro-2,6-dimethyl-4-(3-nitrophenyl)-pyridine-3,5-dicarboxylate, 3-(2-n-butoxyethyl) 5-[3-(4,4-diphenylpiperid-1-yl)-propyl] 1,4-dihydro-2,6-dimethyl-4-(3-nitrophenyl)-pyridine-3,5-dicarboxylate, 3-methyl 5-{3-[4,4-di(4-methoxyphenyl)-piperid-1-yl]propyl} 1,4-dihydro-2,6-dimethyl-4-(3-nitrophenyl)-pyridine-3,5-dicarboxylate, 3-ethyl 5-[3-(4,4-diphenylpiperid-1-yl)-propyl] 1,4-dihydro-2,6-dimethyl-4-(2-trifluoromethylphenyl)-pyridine-3,5-dicarboxylate, 3-methyl 5-[3-(4,4-diphenylpiperid-1-yl)-propyl] 1,4-dihydro-2,6-dimethyl-4-[3-(1,1,2,2-tetrafluoroethoxy)-phenyl]-pyridine-3,5-dicarboxylate, 3-ethyl 5-[3-(4,4-diphenylpiperid-1-yl)-propyl] 1,4-dihydro-2,6-dimethyl-4-(2-difluoromethoxyphenyl)-pyridine-3,5-dicarboxylate, 3-methyl 5-[3-(4,4-dihydroxyphenylpiperid-1-yl)-propyl] 1,4-dihydro-2,6-dimethyl-4-(3-nitrophenyl)-pyridine-3,5-dicarboxylate, 3-methyl 5-[3-(4,4-diphenylpiperid-1-yl)-propyl] 4-(2,3-dichlorophenyl)-1,4-dihydro-2,6-dimethylpyridine-3,5-dicarboxylate, 3-methyl 5-[3-(4,4-diphenylpiperid-1-yl)-propyl] 4-(3-cyanophenyl)-1,4-dihydro-2,6-dimethylpyridine-3,5-dicarboxylate, 3-methyl 5-[3-(4,4-diphenylpiperid-1-yl)-propyl] 1,4-dihydro-2,6-dimethyl-4-(2-methoxyphenyl)-pyridine-3,5-dicarboxylate, 3-methyl 5-[3-(4,4-diphenylpiperid-1-yl)-propyl] 1,4-dihydro-2,6-dimethyl-4-(2-pyridyl)-pyridine-3,5-dicarboxylate, 3-methyl 5-[3-(4,4-diphenylpiperid-1-yl)-propyl] 1,4-dihydro-2,6-dimethyl-4-(5-methyl-2-thienyl)-pyridine-3,5-dicarboxylate, and 3-methyl 5-{3-[4-(4-chlorophenyl)-4-phenylpiperid-1-yl]propyl} 1,4-dihydro-2,6-dimethyl-4-(3-nitrophenyl)-pyridine-3,5-dicarboxylate, and their salts.

The compounds of formula I have a chirality center at the 4-position in the 1,4-dihydropyridine. The invention therefore includes both the enantiomers and, if a further chirality center is present, the diasterisomers, and mixtures and racemates thereof.

The invention furthermore relates to a process for the preparation of the compounds according to the invention and of their salts. The process is characterized in that (a) cinnamic acid derivatives of formula II

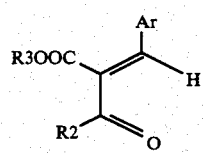

are reacted with enamine derivatives of formula III

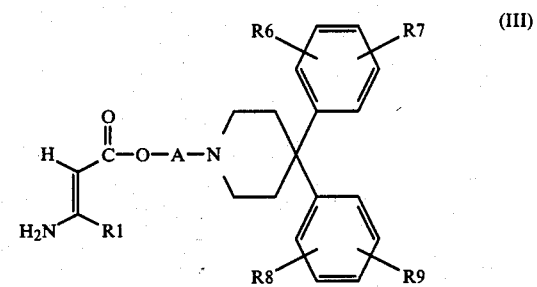

or (b) cinnamic acid derivatives of formula II are reacted with ammonia and β-ketocarboxylic acid derivatives of formula IV

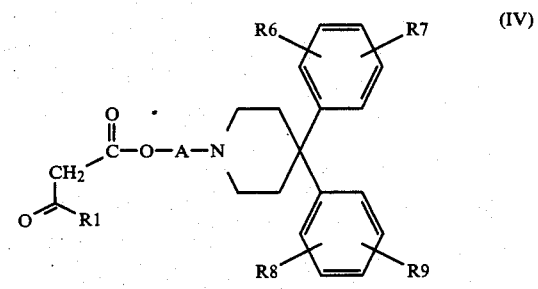

or (c) enamines of the formula V

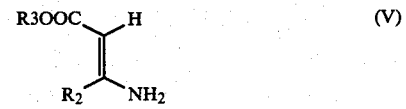

are reacted with benzylidenecarboxylic acid derivatives of formula VI

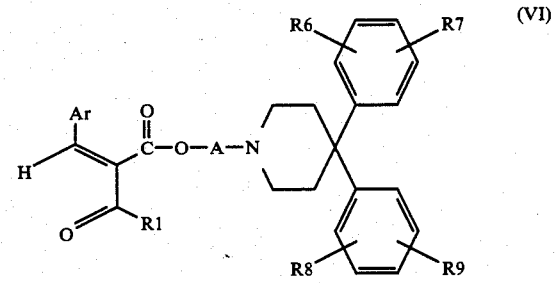

or (d) keto compounds of formula VII

are reacted with ammonia and benzylidenecarboxylic acid derivatives of formula VI, or (e) aldehydes of formula VIII

(VIII)

are reacted with enamines of formula V and β-ketocarboxylic acid derivatives of formula IV, or (f) aldehydes of formula VIII are reacted with enamine derivatives of formula III and keto compounds of formula VII, or (g) 1,4-dihydropyridines of formula IX

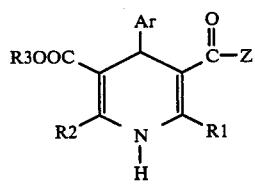

(IX)

are reacted with diaryl compounds of formula X

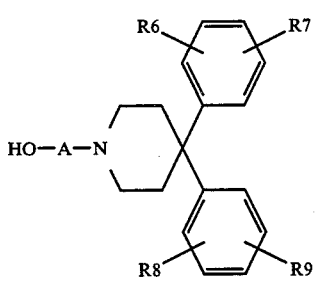

(X)

as such or in the form of their salts. If desired, resulting salts are then converted into free bases, or resulting bases are converted into their salts. In formulas (II) through (X), $R_1$, $R_2$, $R_3$, $R_4$, $R_5$, $R_6$, $R_7$, $R_8$, $R_9$, Y and A have their previously mentioned meanings and Z, together with the carbonyl group to which it is bonded, represents a carboxyl group or a reactive carboxylic acid derivative, such as a carboxylic acid halide. [The contemplated scope of reactive carboxylic acid derivative is readily understood by any organic synthesist.]

The process according to variants a to f is carried out in suitable, preferably inert, organic solvent. Examples of suitable solvents include alcohols, such as ethanol, methanol, isopropanol or tert.-butanol; ethers, such as dioxane, diethyl ether, tetrahydrofuran, glycol monoethyl ether or glycol dimethyl ether; polar solvents, such as dimethylformamide, dimethyl sulfoxide, acetonitrile or hexamethylphosphoric acid triamide, and, in particular, chlorinated hydrocarbons, such as methylene chloride, chloroform or tetrachloroethylene.

The reaction temperatures can be varied within a wide range—depending on the reactivity of the educts. The reaction is generally carried out at temperatures between 20° C. and 150° C., preferably between 20° C. and 100° C. and in particular at the boiling point of the solvent used.

The process can be carried out under normal pressure or under increased pressure, the reaction under normal pressure being the rule. It is possible to apply increased pressure, in particular, for reactions with ammonia.

In carrying out the process according to the invention in variants a to f, the substances participating in the reaction are, as a rule (in each case), employed in molar amounts, but, if desired, an excess (for example of ammonia in variants b and d) can also be employed—depending on reaction conditions.

In carrying out the process according to variant g, reaction conditions similar to those for variants a to f are used, but, if appropriate, additional measures may be necessary—depending on the nature of the substituent Z. For example, when Z represents a hydroxyl group, the reaction is preferably carried out in the presence of a condensing agent which splits off or binds water (such as dicyclohexylcarbodiimide). When Z represents a halogen atom (for example a chlorine atom), the reaction is carried out, if desired, in the presence of a base (for example a tertiary organic amine, such as triethylamine, or an inorganic carbonate, such as sodium carbonate).

The substances according to the invention are isolated and purified in a manner which is known per se, for example by distilling off the solvent in vacuo and recrystallizing the resulting residue from a suitable solvent or subjecting it to one of the customary purification methods, such as column chromatography on a suitable carrier material.

Acid-addition salts are obtained by dissolving the free base in a suitable solvent, for example in a chlorinated hydrocarbon, such as methylene chloride or chloroform, or a low molecular weight aliphatic alcohol (ethanol or isopropanol), containing the desired acid or to which the desired acid is subsequently added.

The salts are obtained by filtration, reprecipitation, precipitation with a non-solvent for the addition salt or evaporation of the solvent.

The obtained salts are readily converted into the free bases by rendering them alkaline, for example with aqueous ammonia solution, and these bases are conventionally converted into acid-addition salts. Pharmacologically-unacceptable acid-addition salts are conventionally converted into pharmacologically-acceptable acid-addition salts.

The starting compounds are known from the literature or are prepared by methods analogous to those known from the literature. The cinnamic acid derivatives II and the benzylidenecarboxylic acid derivatives VI are prepared, for example, by a method analogous to that of G. Jones ["The Knoevenagel Condensation" in Org. Reactions, Volume XV, 204 et seq. (1967)]. The enamine derivatives III and the enamines V are obtainable, for example, by a method analogous to that of A. C. Cope [J. Amer. Chem. Soc. 67, 1017 (1945)]. β-Ketocarboxylic acid derivatives IV and keto compounds VII are prepared in accordance with the method of D. Borrmann ["Umsetzung von Diketen mit Alkoholen, Phenolen und Mercaptanen" ("The Reaction of Diketene with Alcohols, Phenols and Mercaptans") in Houben-Weyl, Methoden der Organischen Chemie (Methods of Organic Chemistry), Volume VII/4, 230 et seq. (1968)] or Y. Oikawa et al. [J. Org. Chem. 43, 2087 (1978)]. The compounds IX are accessible from corresponding starting compounds by variants analogous to process variants a to f. Compounds X are obtainable by reaction of corresponding piperidines (see, for example, German Patent Specification No. 1,936,452) with ω-halogenoalkanols.

The noted preparation processes are mentioned only for illustration, and the preparation of the compounds of formula I according to the invention is not restricted to these processes. Rather, any modification of these processes can be applied in the same manner to the preparation of the compounds according to the invention.

Preferred process variants are variants a and c.

The following preparation examples are intended to illustrate the invention in more detail without limiting it. m.p. denotes melting point and b.p. represents boiling point.

EXAMPLES 1. 3-Methyl 5-[3-(4,4-diphenylpiperid-1-yl)-propyl] 1,4-dihydro-2,6-dimethyl-4-(3-nitrophenyl)-pyridine-3,5 dicarboxylate hydrochloride (Process variant e)

4.53 g of 3-nitrobenzaldehyde, 3.45 g of methyl 3-aminocrotonate and 11.38 g of 3-(4,4-diphenylpiperid-1-yl)propyl acetoacetate in 100 ml of 2-propanol are heated at the boiling point under reflux overnight. The cooled solution is concentrated to dryness and the residue which remains is chromatographed over a silica gel column using ethyl acetate as the eluant. The uniform product fractions leave a solid foamed residue after concentration, the residue is dissolved in methanol, and ethereal hydrochloric acid is added. The solution is concentrated, the solid residue which remains is taken up in a little methanol and the title substance is precipitated by addition of petroleum ether. m.p.: from 135° C. (decomposition); yield: 9.3 g.

The starting compounds are obtained as follows:

(a) 3-(4,4-Diphenylpiperid-1-yl)-propyl acetoacetate 23.6 g of 3-(4,4-diphenylpiperid-1-yl)-propanol are dissolved in 100 ml of absolute toluene, and 16 ml of a 50% strength solution of diketene in acetone are added, with stirring. After the mixture has been left to stand at room temperature for several days (control by thin layer chromatography), it is concentrated, and the residue is dried under a high vacuum. The pale yellow viscous oil which remains is employed for the next stage without further purification.

(b) 3-(4,4-Diphenylpiperid-1-yl)-propanol 40 g of 4,4-diphenylpiperidine, 24.7 g of 3-bromopropanol, 116.4 g of powdered potassium carbonate and about 1 g of potassium iodide are heated at the boiling point under reflux and with vigorous stirring in 500 ml of a 1:1 mixture of dioxane and 1-butanol for about 48 hours. After cooling, the mixture is filtered and the filtrate is concentrated. The oily residue is taken up in ethyl acetate, and the solution is filtered again. After the filtrate has been concentrated to dryness, the title product is obtained as a yellowish oily residue which slowly solidifies as a wax. Yield: 44.8 g. With ethereal hydrochloric acid, the hydrochloride is obtained, and is recrystallized from 2-propanol. m.p.: 226°–227° C.

Alternatively, the starting compound (b) is obtained by heating 352 g of 4,4-diphenylpiperidine, 128 g of sodium hydroxide granules, 2.5 l of methylene chloride, 500 ml of water, 218 g of 3-bromo-1-propanol and catalytic amounts of a phase transfer catalyst (for example benzyltrimethylammonium chloride) at the boiling point under reflux for 10 hours. The organic phase is separated off and washed with water, and the collected aqueous phases are extracted with methylene chloride. After the combined organic phases have been dried with sodium sulfate, the clear brownish solution is evaporated to dryness. The resinous brown residue is taken up in 4.5 l of boiling petroleum ether (boiling range 100° to 140° C.), the insoluble residue is filtered off hot from the solution, and the filtrate is cooled. After being left to stand overnight, the title compound is obtained as the free base in the form of colorless coarse crystals. m.p.: 97° C.; yield: 303 g.

The following starting compounds are obtained analogously:

4-(4,4-diphenylpiperid-1-yl)-butanol, m.p. of the hydrochloride: 209°–212° C., 2-(4,4-diphenylpiperid-1-yl)-2-methylpropanol, m.p.: 115°–116° C., 3-[4,4-di-(4-methoxyphenyl)-piperid-1-yl]-propanol, m.p. of the hydrochloride: 130°–134° C. (contains 1 equivalent of methanol in the crystal), 3-(4,4-diphenylpiperid-1-yl)-2-methyl-2-propanol, m.p. of the hydrochloride: 181°–183° C., 2-(4,4-diphenylpiperid-1-yl)-ethanol, m.p. of the hydrochloride: 197°–199° C.

By reaction of the above alcohols with a solution of diketene analogously to Example 1a, the corresponding acetoacetates are obtained which are further reacted without purification.

(Process variant c)

15.38 g of 3-(4,4-diphenylpiperid-1-yl)-propyl 2-acetyl-3-(3-nitrophenyl)acrylate and 3.45 g of methyl 3-aminocrotonate in 100 ml of 2-propanol are heated at the boiling point under reflux overnight. The cooled solution is evaporated to dryness, the foamed solid residue is taken up in a little methylene chloride, the ethereal hydrochloric acid is added. After renewed concentration to dryness and taking up of the solid residue in a little methylene chloride, ethyl acetate is added until a slight cloudiness persists. After the mixture has been left to stand in a refrigerator, the title compound crystallizes out overnight in the form of fine, slightly yellowish-colored flakes (microscope). m.p.: 230°–231° C. (decomposition); yield: 13.6 g.

Other solvents which are employed for the condensation reaction are: tert.-butanol, dioxane, tetrahydrofuran and chlorinated hydrocarbons. The yields of product are 60 to 80% of theory.

Other salts of title compound 1 which are analogously prepared are, e.g.: hydrobromide: m.p.: 229°–230° C. (decomposition), fine platelets (from ethyl acetate and diisopropyl ether); fumarate: m.p.: 144°–145° C. (decomposition), fine flakes (from ethyl acetate); maleate; m.p.: 151°–152° C. (decomposition), clusters of coarse needles (from ethyl acetate).

The free base of title compound 1 is obtained by concentrating the condensation batch to dryness and taking up the foamed solid residue in a little methylene chloride; after addition of diisopropyl ether until a fine cloudiness remains, the base crystallizes out in the form of fine platelets, after being left to stand in a refrigerator. m.p.: 145°–147° C.

The starting compound 3-(4,4-diphenylpiperid-1-yl)-propyl 2-acetyl-3-(3-nitrophenyl)-acrylate (cis/trans isomer mixture) is obtained as follows:

40.14 g of 3-(4,4-diphenylpiperid-1-yl)-propyl acetoacetate, 15.97 g of 3-nitrobenzaldehyde, 8.0 ml of acetic acid and 0.5 ml of piperidine are heated at the boiling point in 300 ml of benzene using a water separator. After 1.9 ml of water has been separated off, the cooled solution is washed with saturated sodium bicarbonate solution and then with water. After the organic phase has been dried with sodium sulfate, the resulting clear red-brown solution is concentrated to constant weight under a high vacuum. The red-brown viscous residue obtained is employed directly for the condensation, without further purification. Yield: 52 g of crude product. Other entraining agents which are suitable are: toluene and chlorinated hydrocarbons. The yield of crude product is 90 to 100% of theory.

By reacting the free base with an equimolar amount of fumaric acid, the fumarate of the starting compound is obtained; m.p.: from 128° C. (decomposition), clusters of fine needles, from ethyl acetate.

By reaction with ethereal hydrochloric acid, the hydrochloride is obtained: m.p.: 152°–155° C. (fine platelets, from ethyl acetate and diethyl ether).

(Process variant a)

134.6 g of methyl 2-acetyl-3-(3-nitrophenyl)-acrylate, 204.5 g of 3-(4,4-diphenylpiperid-1-yl)-propyl 3-aminocrotonate and 4.5 ml of acetic acid in 2.7 l of anhydrous dioxane are heated at the boiling point under reflux and under a nitrogen atmosphere for 20 hours. After cooling, 45 ml of concentrated hydrochloric acid (37%) are added to the mixture, seed crystals of the title compound 1 are added and the mixture is left to stand at room temperature for 24 hours. The precipitate is filtered off with suction, washed with dioxane and diisopropyl ether and then dried in vacuo at 75° C. The product (270 g) is partitioned between 1.5 l of methylene chloride and aqueous ammonia solution (pH 11), the organic phase is dried over sodium sulfate and the solvent is then distilled off in vacuo. The residue is dissolved in 2.5 l of dioxane, 35 ml of concentrated hydrochloric acid (37% strength) are added, and the mixture is seeded and left to stand for 40 hours. The product which has crystallized out is filtered off with suction, washed with dioxane and then diisopropyl ether, and dried at 100° C. in vacuo. The title substance is obtained as a pale yellow powder (microscope: small needles). m.p.: 198°–200° C.; yield: 246 g.

The starting compound 3-(4,4-diphenylpiperid-1-yl)-propyl 3-aminocrotonate is prepared as follows:

260.5 g of 3-(4,4-diphenylpiperid-1-yl)-propyl acetoacetate in 1.6 l of 2-propanol are stirred overnight with 260 ml of concentrated ammonia solution. The fine, slightly ochre-colored precipitate (which has separated out) is filtered off with suction and washed with cold 2-propanol, with diethyl ether and finally with petroleum ether m.p.: 144°–150° C.; yield: 225 g. After addition of a further 100 ml of concentrated ammonia solution to the filtrate and after the mixture has been left to stand in a refrigerator for several days, a further 12 g of product of identical melting point are obtained.

Alternatively, the starting compound is obtained by passing gaseous ammonia into a solution of 3-(4,4-diphenylpiperid-1-yl)-propyl acetoacetate in 2-propanol, with stirring, until no further precipitate separates out. Yield: about 90% of theory.

2. 3-Methyl 5-[2-(4,4-diphenylpiperid-1-yl)-ethyl]1,4-dihydro-2,6-dimethyl-4-(3-nitrophenyl)-pyridine-3,5-dicarboxylate hydrochloride The title compound of m.p.: from 137° C. (decomposition); yield: 8.5 g, is obtained analogously to Example 1 from 4.53 g of 3-nitrobenzaldehyde, 3.45 g of methyl aminocrotonate and 11 g of 2-(4,4-diphenylpiperid-1-yl)-ethyl acetoacetate in 100 ml of 2-propanol.

3. 3-Methyl 5-[3-(4,4-diphenylpiperid-yl)-propyl] 4-(3-cyanophenyl)-1,4-dihydro-2,6-dimethylpyridine-3,5-dicarboxylate hydrochloride The title compound of m.p. 136°–146° C. (slow deliquescense, amorphous, precipitated in petroleum ether); yield: 5.9 g, is obtained analogously to Example 1 from 3.93 g of 3-cyanobenzaldehyde, 3.45 g of methyl 3-aminocrotonate and 11.38 g of 3-(4,4-diphenylpiperid-1-yl)-propyl acetoacetate in 80 ml of tert.-butanol.

4. 3-Methyl 5-[2-(4,4-diphenylpiperid-1-yl)-2-methylpropyl] 1,4-dihydro-2,6-dimethyl-4-(3-nitrophenyl)pyridine-3,5-dicarboxylate hydrochloride The title compound (yield: 13.6 g) of m.p. from 155° C. (slow deliquescence, amorphous, precipitated from petroleum ether) is obtained analogously to Example 1 from 15.8 g of 2-(4,4-diphenylpiperid-1-yl)-2-methylpropyl 2-acetyl-3-(3-nitrophenyl)-acrylate and 3.45 g of methyl 3-aminocrotonate in 100 ml of tetrahydrofuran after a reaction time of 12 hours.

5. 3-Ethyl 5-[3-(4,4-diphenylpiperid-1-yl)-propyl] 1,4-dihydro-2,6-dimethyl-4-(3-nitrophenyl)-pyridine-3,5-dicarboxylate hydrochloride The title compound (yield: 29.7 g) of m.p. 230°–232° C. (fine angular cyrstals, from acetonitrile and diethyl ether) is obtained analogously to Example 1 from 13.16 g of ethyl 2-acetyl-3-(3-nitrophenyl)-acrylate and 18.91 g of 3-(4,4-diphenylpiperid-1-yl)-propyl 3-aminocrotonate in 100 ml of tetrahydrofuran after a reaction time of 6 hours.

6. 3-Methyl 5-[3-(4,4-diphenylpiperid-1-yl)-propyl] 1,4-dihydro-2,6-dimethyl-4-[3-(1,1,2,2-tetrafluoroethoxy)-phenyl]-pyridine-3,5-dicarboxylate hydrochloride The title compound (yield: 57 g) of m.p. 189°–192° C. is obtained analogously to Example 1 from 40.33 g of methyl 2-acetyl-3-[3-(1,1,2,2-tetrafluoroethoxy)-phenyl]-acrylate and 37.85 g of 3-(4,4-diphenylpiperid-1-yl)-propyl 3-aminocrotonate in 400 ml of tetrahydrofuran and 0.5 ml of glacial acetic acid after a reaction time of 14 hours.

7. 3-Methyl 5-[2-(4,4-diphenylpiperid-1-yl)-ethyl] 1,4-dihydro-2,6-dimethyl-4-[3-(1,1,2,2-tetrafluoroethoxy)-phenyl]-pyridine-3,5-dicarboxylate hydrochloride The title compound (yield: 6.2 g) of m.p. 130°–140° C. (slow deliquescence, amorphous, precipitated from petroleum ether and diethyl ether 1:1) is obtained analogously to Example 1 from 4.03 g of methyl 2-acetyl-3-[3(1,1,2,2-tetrafluoroethoxy)-phenyl]-acrylate and 3.4 g of 2-(4,4-diphenylpiperid-1-yl)-ethyl 3-aminocrotonate in 80 ml of 2-propanol after a reaction time of 8 hours.

8. 3-(2-Methoxyethyl) 5[2-(4,4-diphenylpiperid-1-yl)ethyl] 1,4-dihydro-2,6-dimethyl-4-(3-nitrophenyl)pyridine-3,5-dicarboxylate fumarate The title compound (yield: 3.7 g) of m.p. from 130° C. (slow deliquescence, fine platelets, from ethyl acetate and diethyl ether) is obtained analogously to Example 1 from 4.99 g of 2-(4,4-diphenylpiperid-1-yl)-ethyl 2-acetyl-3-(3-nitrophenyl)-acrylate and 1.6 g of 2-(2-methoxyethyl)-3-aminocrotonate in 60 ml of tetrahydrofuran and 0.5 ml of glacial acetic acid after a reaction time of 4 hours.

9. 3-(2-Methoxyethyl) 5-[3-(4,4-diphenylpiperid-1-yl)propyl] 1,4-dihydro-2,6-dimethyl-4-(3-nitrophenyl)pyridine-3,5-dicarboxylate fumarate The title compound (yield: 5.3 g) of m.p. 184°–185° C. (angular flakes, from ethyl acetate and diethyl ether) is obtained analogously to Example 1 from 5.12 g of 3-(4,4-diphenylpiperid-1-yl)-propyl 2-acetyl-3-(3-nitrophenyl)-acrylate and 1.6 g of 2-(2-methoxyethyl)-3-aminocrotonate in 80 ml of tert.-butanol after a reaction time of 5 hours.

10. 3-Methyl 5-{3-[4,4-di-(4-methoxyphenyl)-piperid-1-yl]-propyl} 1,4-dihydro-2,6-dimethyl-4-(3-nitrophenyl)-pyridine-3,5-dicarboxylate hydrochloride The title compound (yield: 4.9 g) of m.p. from 138° C. (slow deliquescence, amorphous, precipitated in petroleum ether) is obtained analogously to Example 1 from 4.4 g of 3-[4,4-di-(4-methoxyphenyl)-piperid-1-yl]propyl acetoacetate, 1.15 g of methyl 3-aminocrotonate and 1.51 g of 3-nitrobenzaldehyde in 60 ml of tert.-butanol after a reaction time of 12 hours.

11. 3-Methyl 5-[4-(4,4-diphenylpiperid-1-yl)-butyl] 1,4-dihydro-2,6-dimethyl-4-(3-nitrophenyl)-pyridine-3,5-dicarboxylate fumarate The title compound (yield: 3.9 g) of m.p. 123°–126° C. (fine needles, from ethyl acetate and methylene chloride) is obtained analogously to Example 1 from 3.94 g of 4-(4,4-diphenylpiperid-1-yl)-butyl acetoacetate, 1.15 g of methyl 3-aminocrotonate and 1.51 g of 3-nitrobenzaldehyde in 80 ml of tert.-butanol after a reaction time of 6 hours.

12. 3-Methyl 5-[1,1-dimethyl-2-(4,4-diphenylpiperid-1-yl)-ethyl] 1,4-dihydro-2,6-dimethyl-4-(3-nitrophenyl)pyridine-3,5-dicarboxylate hydrochloride The title compound (yield: 11.3 g) of m.p. from 148° C. (slow deliquescence, amorphous, precipitated from petroleum ether) is obtained analogously to Example 1 from 15.8 g of 1,1-dimethyl-2-(4,4-diphenylpiperid-1-yl)-ethyl 2-acetyl-3-(3-nitrophenyl)-acrylate and 3.45 g of methyl 3-aminocrotonate in 120 ml of 2-propanol after a reaction time of 15 hours.

13. 3-Ethyl 5-[3-(4,4-diphenylpiperid-1-yl)-propyl] 1,4-dihydro-2,6-dimethyl-4-(2-difluoromethoxyphenyl)-pyridine-3,5-dicarboxylate hydrochloride The title compound (yield: 2.8 g) of m.p. from 126° C. (slow deliquescence, amorphous, precipitated from petroleum ether and diethyl ether 1:1) is obtained analogously to Example 1 from 3.8 g of 3-(4,4-diphenylpiperid-1-yl)-propyl 2-acetyl-3-(2-difluoromethoxyphenyl)-acrylate and 1.3 g of ethyl 3-aminocrotonate in 60 ml of tert.butanol after a reaction time of 20 hours.

14. 1,4-Dihydro-2,6-dimethyl-4-(3-nitrophenyl)-pyridine-3,5-dicarboxylic acid 3-[3-(4,4-diphenylpiperid-1-yl)-propyl]ester 6.8 g of 3-(2-cyanoethyl) 5-[3-(4,4-diphenylpiperid-1-yl)-propyl] 1,4-dihydro-2,6-dimethyl-4-(3-nitrophenyl)-pyridine-3,5-dicarboxylate hydrochloride are stirred with 40 ml of 0.5N sodium hydroxide solution and 100 ml of dioxane at room temperature for 3 hours. After most of the dioxane has been distilled off, 15 ml of 2N hydrochloric acid are added to the residue. The resulting milky/cloudy solution is extracted 4 times with 100 ml of chloroform/n-butanol (3:1) each time, and the combined organic phase is washed with 50 ml of saturated sodium chloride solution. The organic phase is concentrated to dryness, and the solid residue is recrystallized from chloroform/methanol (1:1). m.p. 192°–195° C. (decomposition); yield: 5.4 g.

The starting compound 3-(2-cyanoethyl) 5-[3-(4,4-diphenylpiperid-1-yl)-propyl] 1,4-dihydro-2,6-dimethyl-4-(3-nitrophenyl)-pyridine-3,5-dicarboxylate is obtained as follows:

8.1 g of 2-cyanoethyl 2-acetyl-3-(3-nitrophenyl)acrylate and 10.6 g of 3-(4,4-diphenylpiperid-1-yl)-propyl 3-aminocrotonate are heated at the boiling point under reflux in 120 ml of 2-propanol and 0.5 ml of glacial acetic acid for 4 hours. After most of the solvent has been distilled off and 2 portions of 50 ml of toluene each have been added, the residue is concentrated to dryness. The residue, which has foamed as a solid, is taken up in isopropanol, and diethyl ether is added to the clear solution until the resulting cloudiness first persists. After the mixture has been left to stand in a refrigerator, the starting compound crystallizes out in the form of fine platelets. m.p.: 158°–160° C.; yield: 14.3 g.

With ethereal hydrochloric acid, the hydrochloride of the starting compound is obtained, and is recrystallized from methylene chloride/methanol. m.p.: 184°–194° C. (slow deliquescence).

15. 3-Ethyl 5-[3-(4,4-diphenylpiperid-1-yl)-propyl] 1,4-dihydro-2,6-dimethyl-4-[3-(1,1,2,2-tetrafluoroethoxy)-phenyl]-pyridine-3,5-dicarboxylate hydrochloride The title compound (yield: 48.9 g) of m.p. 196°–197° C. (decomposition, from methylene chloride and diisopropyl ether) is obtained analogously to Example 1 from 22.2 g of 3-(1,1,2,2-tetrafluoroethoxy)-benzaldehyde, 12.9 g of ethyl 3-aminocrotonate and 37.9 g of 3-(4,4-diphenylpiperid-1-yl)-propyl acetoacetate in 280 ml of tert.-butanol after a reaction time of 14 hours.

16. 3-Ethyl 5-[3-(4,4-diphenylpiperid-1-yl)-propyl] 1,4-dihydro-2,6-dimethyl-4-(3-difluoromethoxyphenyl)-pyridine-3,5-dicarboxylate hydrochloride The title compound (yield: 5.1 g) of m.p. 197°–198° C. (fine platelets from methylene chloride and ethyl acetate) is obtained analogously to Example 1 from 1.6 g of 3-difluoromethoxybenzaldehyde, 1.3 g of ethyl 3-aminocrotonate and 3.8 g of 3-(4,4-diphenylpiperid-1-yl)-propyl acetoacetate in 80 ml of tetrahydrofuran after a reacton time of 4 hours.

17. 3-Methyl 5-[3-(4,4-diphenylpiperid-1-yl)-propyl] 4-(2,3-dichlorophenyl)-1,4-dihydro-2,6-dimethylpyridine-3,5-dicarboxylate hydrochloride The title compound (yield: 4.2 g) of m.p. 228°–230° C. (fine needles from methanol and ethyl acetate) is obtained analogously to Example 1 from 2.72 g of methyl 2-acetyl-3-(2,3-dichlorophenyl)-acrylate and 3.79 g of 3-(4,4-diphenylpiperid-1-yl)-propyl 3-aminocrotonate in 100 ml of 2-propanol after a reaction time of 7 hours.

18. 3-Methyl 5-[3-(4,4-diphenylpiperid-1-yl)-propyl] 4-(2,1,3-benzoxadiazol-4-yl)-1,4-dihydro-2,6-dimethylpyridine-3,5-dicarboxylate hydrochloride The title compound (yield: 4.1 g) of m.p. 208°–210° C. (fine lumpy crystals from ethyl acetate and methylene chloride) is obtained analogously to Example 1 from 2.5 g of methyl 2-acetyl-3-(2,1,3-benzoxadiazol-4-yl)-acrylate and 3.8 g of 3-(4,4-diphenyl-piperid-1-yl)-propyl 3-aminocrotonate in 60 ml of tetrahydrofuran and 0.5 ml of acetic acid after a reaction time of 4 hours.

19. 3-Methyl 5-[3-(4,4-diphenylpiperid-1-yl)-propyl] 1,4-dihydro-2,6-dimethyl-4-(3-fluorophenyl)-pyridine-3,5-dicarboxylate hydrochloride The title compound (yield: 4.8 g) of m.p. 213°–216° C. (fine, angular crystals from methylene chloride and diisopropyl ether) is obtained analogously to Example 1 from 2.44 g of methyl 2-acetyl-3-(3-fluorophenyl)-acrylate and 4.39 g of 3-(4,4-diphenylpiperid-1-yl)-propyl 3-aminocrotonate in 50 ml of tetrahydrofuran after a reaction time of 5 hours.

20. 3-Methyl 5-[3-(4,4-diphenylpiperid-1-yl)-propyl] 1,4-dihydro-2,6-dimethyl-4-(2-trifluoromethylphenyl)-pyridine-3,5-dicarboxylate hydrochloride The title compound (yield: 4.2 g) of m.p. 158°–162° C. (fine, cubical crystals from methylene chloride and diisopropyl ether) is obtained analogously to Example 1 from 2.7 g of methyl 2-acetyl-3-(2-trifluoromethylphenyl)-acrylate and 4.4 g of 3-(4,4-diphenylpiperid-1-yl)-propyl 3-aminocrotonate in 60 ml of tert.-butanol after a reaction time of 4 hours.

21. 3-Ethyl 5-[3-(4,4-diphenylpiperid-1-yl)-propyl] 4-(2-cyanophenyl)-1,4-dihydro-2,6-dimethylpyridine-3,5-dicarboxylate hydrochloride The title compound (yield: 8.4 g) of m.p. 178°–181° C. (fine needles from ethyl acetate and methylene chloride) is obtained analogously to Example 1 from 3.93 g of 2-cyanobenzaldehyde, 3.45 g of methyl 3-aminocrotonate and 11.38 g of 3-(4,4-diphenyl-piperid-1-yl)-propyl acetoacetate in 80 ml of 2-propanol after a reaction time of 10 hours.

22. 3-Methyl 5-[3-(4,4-diphenylpiperid-1-yl)-propyl] 4-(2-chlorophenyl)-1,4-dihydro-2,6-dimethylpyridine-3,5-dicarboxylate hydrochloride The title compound (yield: 3.3 g) of m.p. 150° C. (decomposition) (fine, needles from methylene chloride and diisopropyl ether) is obtained analogously to Example 1 from 3.6 g of methyl 2-acetyl-3-(2-chlorophenyl)-acrylate and 5.7 g of 3-(4,4-diphenylpiperid-1-yl)-propyl 3-aminocrotonate in 60 ml of tetrahydrofuran and 0.5 ml of acetic acid after a reaction time of 8 hours.

COMMERCIAL USEFULNESS

The compounds of the formula I according to the invention and their salts have useful properties which render them commercially useful. In particular, they are active vasodilators with properties as coronary therapeutics. The pharmacological activity of the compounds according to the invention, which is coupled with low toxicity, manifests itself in particular in a reduction in blood pressure which starts slowly, is powerful and lasts a long time. Moreover, the compounds according to the invention have peripheral, coronary, cerebral and renal vasodilating properties and salidiuretic properties.

In their excellent activity, which is coupled with low toxicity and absence of substantial side effects, the compounds according to the invention differ in a surprising and advantageous manner from prior art compounds. Examples of advantageous properties are: slow onset of reduction in blood pressure, the degree of reduction in blood pressure, the long period which the reduction in blood pressue lasts, the good ease of control of the reduction in blood pressure, the only slight increase in heart rate (which disappears on repeated administration), the excellent bioavailability, the wide therapeutic range, the absence of side effects on the central nervous system, the absence of kinetic interactions with other substances, the absence of tolerance development, the balanced physical properties and the high stability.

The excellent activity of the compounds of formula I according to the invention and their salts enables them to be used in human medicine, possible indications being, in particular, primary (essential) and secondary hypertension of all degrees of severity, coronary heart diseases (coronary insufficiency, angina pectoris, myocardial infarction, etc.), disturbances in peripheral and cerebral circulation (cerebral apoplexy, temporary disturbances in cerebral circulation, narrowing of the renal artery, etc.), cardiac insufficiency and diseases based on an increased retention of water and sodium.

The invention thus furthermore relates to a method for treating mammals, in particular humans, suffering from one of the mentioned diseases. The method is characterized by administering a therapeutically-effective and pharmacologically-acceptable amount of one or more compounds of formula I to a thus-afflicted sick individual.

The invention also relates to the compounds of formula I and particularly for use in the treatment of the indicated conditions and diseases. The compounds are primarily useful for treating non-cancerous conditions, but nothing is known that would preclude the use of compounds of formula I or their salts in conjunction or combination with cancer therapy.

The invention likewise relates to the use of compounds of formula I in the preparation of medicaments which are employed for combating the noted diseases.

The invention furthermore relates to medicaments containing one or more compounds of formula I.

The medicaments are prepared by processes which are known per se and are familiar to the expert. As medicaments, the pharmacologically-active compounds (=active compounds) according to the invention are employed either or such or, preferably, in combination with suitable pharmaceutical auxiliaries in the form of tablets, coated tablets, capsules, suppositories, plasters (for example as TTS), emulsions, suspensions or solutions, the content of active compound advantageously being between 0.1 and 95% by weight.

The expert is familiar with what auxiliaries are suitable for the desired medicament formulations on the basis of his expert knowledge. In addition to solvents, gelling agents, suppository bases, tabletting auxiliaries and other active compound excipients, it is possible to use, for example, antioxidants, dispersing agents, emulsifiers, antifoaming agents, flavor correctants, preservatives, solubilizing agents, dyestuffs or, in particular, permeation promoters and complexing agents (for example cyclodextrins).

The active compounds are administered orally or parenterally (particular perlingually, intravenously or percutaneously).

In general, it has proved advantageous in human medicine to administer the active compound or compounds when these are administered orally, in a daily dose of about 0.01 to about 10, preferably 0.05 to 5, mg/kg of body weight, if desired in the form of several, preferably 1 to 4, individual doses, to achieve the desired results. In the case of parenteral treatment, similar or (especially when the active compounds are administered intravenously) as a rule lower doses can be used. With a dosage increasing from initially small amounts, a lower dose is administered at the start of the treatment and this is then slowly changed to a higher dose. When the desired therapeutic result is achieved, the dose is reduced again to a lower dose.

The particular optimum dosage required and the mode of administration of the active compounds is easily determined by any expert on the basis of his expert knowledge.

When compounds according to the invention and/or their salts are employed for the treatment of mentioned diseases, the pharmaceutical formulations optionally contain one or more other pharmacologically-active constituents from other groups of medicaments, such as other vasodilators, antihypertensives, α-receptor blockers, β-receptor blockers, ACE-inhibitors, nitro-compounds, cardiotonics, diuretics, saluretics, alkaloids, etc., such as nifedipine, dihydralazine, prazosine, propranolol, labetalol, captopril, isosorbide dinitrate, digoxin, mefruside, clopamide, spironolactone, chlorthalidone, furosemide, polythiazide, hydrochlorothiazide, reserpine, dihydroergocristine, rescinnamine, Rauwolfia total alkaloids, etc.

PHARMACOLOGY

The antihypertensive activity of the compounds according to the invention can be demonstrated on the model of spontaneously-hypertensive rats.

To determine the antihypertensive action, the compounds listed below are administered once daily, by means of a stomach tube, on four successive days in the doses mentioned to (in each case) 6 rats (strain SH/N/Ibm/Bm ♂, 250 to 350 g) with hypertension of genetic origin (RR>180 mmHg). The blood pressure is, in each case, measured 6 and, if appropriate, 2 or 24 hours after administration of the substance.

The blood pressure measurement is carried out in a heated chamber at 36° C. in order to achieve better circulation in the tail artery. For this, the animals are transferred to perforated sheet metal cages, and the measurement is made from 20 to 40 minutes after warming up has been started. To measure the systolic arterial pressure, an annular cuff with an inflatable rubber membrane (for suppressing circulation) and an annular piezocrystal transducer (to record pulse waves) are pushed onto the tail. When the blood stream has been suppressed in the tail artery, the cuff pressure is reduced continuously. Return of the pulse waves as the pressure is reduced is recognized and expressed automatically as the systolic blood pressure [Bühler, R., et al.: Microprocessor-based automation of blood pressure measurement in the conscious rat. Proceedings of the 4th international symposium on rats with spontaneous hypertension and related studies, Rascher, R., et al. (eds.), Schattauer, Verlag, Stuttgart, New York, 1982, pages 410–413]. The pulse signals and pressure course are recorded graphically for evaluation.

For acclimatization to the measurement process, the animals are trained for 14 days before the substance is tested. In the second week of training, blood pressure prevalues are recorded. The groups of animals receiving the substance are tested against a control group.

In the table which follows, the compounds investigated are labelled by serial numbers, which are allocated as follows:

| Serial No. | Name of the compound |
|---|---|
| 1 | 3-Methyl 5-[3-(4,4-diphenylpiperid-1-yl)-propyl] 1,4-dihydro-2,6-dimethyl-4-(3-nitrophenyl)-pyridine-3,5-dicarboxylate hydrochloride |
| 2 | 3-Methyl 5-[2-(4,4-diphenylpiperid-1-yl)-ethyl] 1,4-dihydro-2,6-dimethyl-4-(3-nitrophenyl)-pyridine-3,5-dicarboxylate hydrochloride |
| 3 | 3-Methyl 5-[3-(4,4-diphenylpiperid-1-yl)-propyl] 4-(3-cyanophenyl)-1,4-dihydro-2,6-dimethylpyridine-3,5-dicarboxylate hydrochloride |
| 4 | 3-Methyl 5-[2-(4,4-diphenylpiperid-1-yl)-2-methyl-propyl] 1,4-dihydro-2,6-dimethyl-4-(3-nitrophenyl)-pyridine-3,5-dicarboxylate hydrochloride |
| 5 | 3-Ethyl 5-[3-(4,4-diphenylpiperid-1-yl)-propyl] 1,4-dihydro-2,6-dimethyl-4-(3-nitrophenyl)-pyridine-3,5-dicarboxylate hydrochloride |
| 6 | 3-Methyl 5-[3-(4,4-diphenylpiperid-1-yl)-propyl] 1,4-dihydro-2,6-dimethyl-4-[3-(1,1,2,2-tetrafluoroethoxy)-phenyl]-pyridine-3,5-dicarboxylate hydrochloride |
| 7 | 3-(2-Methoxyethyl) 5-[2-(4,4-diphenylpiperid-1-yl)-ethyl] 1,4-dihydro-2,6-dimethyl-4-(3-nitrophenyl)-pyridine-3,5-dicarboxylate fumarate |
| 8 | 3-(2-Methoxyethyl) 5-[3-(4,4-diphenylpiperid-1-yl)-propyl] 1,4-dihydro-2,6-dimethyl-4-(3-nitrophenyl)-pyridine-3,5-dicarboxylate fumarate |
| 9 | 3-Methyl 5-{3-[4,4-di-(4-methoxyphenyl)-piperid-1-yl]-propyl} 1,4-dihydro-2,6-dimethyl-4-(3-nitro-phenyl)-pyridine-3,5-dicarboxylate hydrochloride |
| 10 | 3-Methyl 5-[4-(4,4-diphenylpiperid-1-yl)-butyl] 1,4-dihydro-2,6-dimethyl-4-(3-nitrophenyl)-pyridine-3,5-dicarboxylate fumarate |
| 11 | 3-Methyl 5-[1,1-dimethyl-2-(4,4-diphenylpiperid-1-yl)-ethyl] 1,4-dihydro-2,6-dimethyl-4-(3-nitrophenyl)-pyridine-3,5-dicarboxylate hydrochloride |
| 12 | 3-Ethyl 5-[3-(4,4-diphenylpiperid-1-yl)-propyl] 1,4-dihydro-2,6-dimethyl-4-(2-difluoromethoxyphenyl)-pyridine-3,5-dicarboxylate hydrochloride |
| 13 | 3-Ethyl 5-[3-(4,4-diphenylpiperid-1-yl)-propyl] 1,4-dihydro-2,6-dimethyl-4-(3-difluoromethoxy phenyl)-pyridine-3,5-dicarboxylate hydrochloride |
| 14 | 3-Methyl 5-[3-(4,4-diphenylpiperid-1-yl)-propyl] 4-(2,3-dichlorophenyl)-1,4-dihydro-2,6-dimethylpyridine-3,5-dicarboxylate hydrochloride |
| 15 | 3-Methyl [3-(4,4-diphenylpiperid-1-yl)-propyl] 4-(2,1,3-benzoxadiazol-4-yl)-1,4-dihydro-2,6-dimethylpyridine-3,5-dicarboxylate hydrochloride |
| 16 | 3-Methyl 5-[3-(4,4-diphenylpiperid-1-yl)-propyl] 1,4-dihydro-2,6-dimethyl-4-(3-fluorophenyl)-pyridine-3,5-dicarboxylate hydrochloride |
| 17 | 3-Methyl 5-[3-(4,4-diphenylpiperid-1-yl)-propyl] 1,4-dihydro-2,6-dimethyl-4-(2-trifluoromethylphenyl)-pyridine-3,5-dicarboxylate hydrochloride |
| 18 | 3-Ethyl 5-[3-(4,4-diphenylpiperid-1-yl)-propyl] 4-(2-cyanophenyl)-1,4-dihydro-2,6-dimethyl pyridine-3,5-dicarboxylate hydrochloride |
| 19 | 3-Methyl 5-[3-(4,4-diphenylpiperid-1-yl)-propyl] 4-(2-chlorophenyl)-1,4-dihydro-2,6-dimethylpyridine-3,5-dicarboxylate hydrochloride |

Table I shows the percentage reduction in blood pressure (BP) following oral administration to rats for the representatives of the compounds according to the invention.

The invention, its different aspects and its advantages are readily understood from the preceding description. It is apparent that various changes can be made in the syntheses, structures, intermediates, compositions and uses without departing from the spirit and scope of the invention or sacrificing its material advantages. The processes, products, dosage forms, methods of administration and uses hereinbefore described are merely illustrative of preferred embodiments of the invention.

TABLE I

% change (BP) in genetically hypertensive rats following a single daily oral administration on four successive days (N = 6/dose); the dose in mg/kg is calculated on the free base.

| Serial No. | Dose ($\mu$mol/ kg) | (mg/kg) | BP (% changes vs. control) mean values of the given points of time of measurement | | |
|---|---|---|---|---|---|
| | | | 2 h (1st + 4th day) | 6 h (1st to 4th day) | 24 h (1st + 3rd day) |
| 1 | 5 | 3.05 | −47 | −30 | −7 |
| | 10 | 6.09 | −50 | −37 | −9 |
| | 25 | 15.24 | −48 | −45 | −25 |
| 2 | 25 | 14.89 | −51 | −36 | −2 |
| 3 | 25 | 14.74 | −48 | −41 | −19 |
| 4 | 25 | 15.60 | −51 | −44 | −25 |
| 5 | 10 | 6.24 | −51 | −41 | −20 |
| 6 | 25 | 17.02 | −21 | −21 | −10 |
| 7 | 25 | 15.99 | −44 | −33 | 0 |
| 8 | 25 | 16.34 | −48 | −28 | −5 |
| 9 | 10 | 6.70 | −53 | −45 | −14 |
| 10 | 10 | 6.24 | −40 | −18 | −2 |
| 11 | 5 | 3.12 | −54 | −33 | −15 |
| 12 | 25 | 16.12 | −31 | −11 | +4 |
| 13 | 25 | 16.12 | −41 | −29 | −6 |
| 14 | 25 | 15.84 | −49 | −43 | −30 |
| 15 | 25 | 15.17 | −49 | −41 | −16 |
| 16 | 25 | 14.57 | −46 | −38 | −7 |
| 17 | 25 | 15.82 | −44 | −30 | −17 |
| 18 | 25 | 15.09 | −37 | −25 | −1 |
| 19 | 25 | 14.98 | −43 | −28 | −2 |

What is claimed is:
1. A compound of formula I

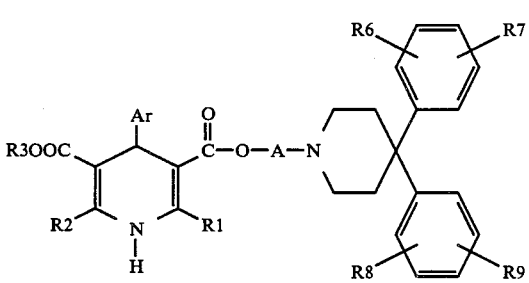

wherein Ar represents a ring of the formula

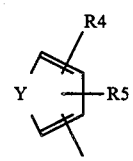

in which Y denotes vinylene (—CH=CH—), or a group of the formula

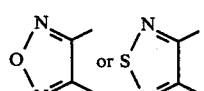

$R_1$, $R_2$ and $R_3$ are identical or different and denote hydrogen, $C_1$–$C_6$-alkyl, $C_3$–$C_7$-alkoxyalkyl, aryl, aryl-$C_1$–$C_6$-alkyl or aryloxy-$C_1$–$C_6$-alkyl, $R_4$ and $R_5$ are identical or different and denote hydrogen, hydroxyl, halogen, nitro, cyano, trifluoromethyl, $C_1$–$C_4$-alkyl, $C_1$–$C_4$-alkoxy, $C_1$–$C_4$-alkoxy which is completely or partly substituted by fluorine, $C_1$–$C_4$-alkoxycarbonyl, $C_2$–$C_5$-acyl, amino or mono- or di-$C_1$–$C_4$-alkylamino, $R_6$, $R_7$, $R_8$ and $R_9$ are identical or different and denote hydrogen, hydroxyl, halogen, $C_1$–$C_4$-alkyl, $C_1$–$C_4$-alkoxy, amino, mono- or di-$C_1$–$C_4$-alkylamino, $C_1$–$C_4$-alkoxy which is completely or partly substituted by fluorine, and A denotes straight-chain or branched $C_2$–$C_5$-alkylene, which is optionally substituted by $C_1$–$C_4$-alkoxy or aryl;

or a salt thereof.

2. A compound of formula I according to claim 1, wherein

Y denotes vinylene (—CH=CH—), and $R_1$, $R_2$, $R_3$, $R_4$, $R_5$, $R_6$, $R_7$, $R_8$, $R_9$ and A have the meanings given in claim 1;

or a salt thereof.

3. A compound of formula I according to claim 1, wherein

Y denotes

$R_4$ and $R_5$ denote hydrogen and $R_1$, $R_2$, $R_3$, $R_6$, $R_7$, $R_8$, $R_9$ and A have the meanings given in claim 1;

or a salt thereof.

4. A compound according to one of claims 1 to 3, wherein $R_1$ denotes $C_1$–$C_4$-alkyl;

$R_2$ denotes $C_1$–$C_4$-alkyl;

$R_3$ denotes $C_1$–$C_4$-alkyl or $C_3$–$C_5$-alkoxyalkyl;

$R_4$ denotes hydrogen, chlorine, nitro, methyl or methoxy;

$R_5$ denotes hydrogen, chlorine, fluorine, nitro, cyano, methyl, methoxy, difluoromethoxy, 1,1,2,2-tetrafluoroethoxy, trifluoromethyl or acetyl;

$R_6$ denotes hydrogen or methoxy;

$R_7$ denotes hydrogen, hydroxyl, chlorine, methyl, methoxy, difluoromethoxy or 1,1,2,2-tetrafluoroethoxy;

$R_8$ denotes hydrogen or methoxy;

$R_9$ denotes hydrogen, hydroxyl, chlorine, methyl, methoxy, difluoromethoxy or 1,1,2,2-tetrafluoroethoxy; and A denotes ethylene or propylene; or a salt thereof.

5. A compound according to one of claims 1 to 3, wherein $R_1$ denotes methyl;

$R_2$ denotes methyl;

$R_3$ denotes methyl, ethyl or methoxyethyl;

$R_4$ denotes hydrogen;

$R_5$ denotes hydrogen, chlorine, fluorine, nitro, cyano, methyl, methoxy, difluoromethoxy, 1,1,2,2-tetrafluoroethoxy or trifluoromethyl;

$R_6$ denotes hydrogen;

$R_7$ denotes hydrogen, hydroxyl, chlorine, methyl, methoxy, difluoromethoxy or 1,1,2,2-tetrafluoroethoxy;

R$_8$ denotes hydrogen;
R$_9$ denotes hydrogen, hydroxyl, chlorine, methyl, methoxy, difluoromethoxy or 1,1,2,2-tetrafluoroethoxy; and A denotes ethylene or propylene;
or a salt thereof.

6. A compound according to claim 2, wherein
R$_1$ denotes methyl;
R$_2$ denotes methyl;
R$_3$ denotes methyl, ethyl or methoxyethyl;
R$_4$ denotes hydrogen or chlorine;
R$_5$ denotes hydrogen, chlorine, fluorine, nitro, cyano, difluoromethoxy, 1,1,2,2-tetrafluoroethoxy or trifluoromethyl;
R$_6$ denotes hydrogen;
R$_7$ denotes hydrogen or methoxy;
R$_8$ denotes hydrogen;
R$_9$ denotes hydrogen or methoxy; and
A denotes ethylene, propylene, butylene, 1,1-dimethylethylene or 2,2-dimethylethylene;
or a salt thereof.

7. A compound according to claim 1, wherein
Ar denotes phenyl, 2-nitrophenyl, 3-nitrophenyl, 2-cyanophenyl, 3-cyanophenyl, 2-(1,1,2,2-tetrafluoroethoxy)-phenyl, 3-(1,1,2,2-tetrafluoroethoxy)-phenyl, 2-difluoromethoxyphenyl, 3-difluoromethoxyphenyl, 2-chlorophenyl, 3-chlorophenyl, 2,3-dichlorophenyl, 2-fluorophenyl, 3-fluorophenyl, 2-trifluoromethylphenyl or 3-trifluoromethylphenyl;
R$_1$ denotes methyl;
R$_2$ denotes methyl;
R$_3$ denotes methyl, ethyl or methoxyethyl;
R$_6$ denotes hydrogen;
R$_7$ denotes hydrogen or methoxy;
R$_8$ denotes hydrogen;
R$_9$ denotes hydrogen or methoxy; and
A denotes ethylene, propylene, butylene, 1,1-dimethylethylene or 2,2-dimethylethylene;
or a salt thereof.

8. A compound according to claim 3, wherein
R$_1$ denotes methyl;
R$_2$ denotes methyl;
R$_3$ denotes methyl, ethyl or methoxyethyl;
R$_4$ denotes hydrogen;
R$_5$ denotes hydrogen;
R$_6$ denotes hydrogen;
R$_7$ denotes hydrogen or methoxy;
R$_8$ denotes hydrogen;
R$_9$ denotes hydrogen or methoxy; and
A denotes ethylene, propylene, butylene, 1,1-dimethylethylene or 2,2-dimethylethylene;
or a salt thereof.

9. A compound according to claim 1, wherein
Ar denotes 2-nitrophenyl or 3-nitrophenyl;
R$_1$, and R$_2$ and R$_3$ are identical or different and denote C$_1$-C$_6$-alkyl or C$_3$-C$_7$-alkoxyalkyl;
A represents straight-chain or branched C$_2$-C$_5$-alkylene;
and each of R$_6$, R$_7$, R$_8$ and R$_9$ denotes hydrogen;
or a salt thereof.

10. A compound according to claim 1, wherein
Ar denotes 2-nitrophenyl or 3-nitrophenyl;
R$_1$ denotes methyl;
R$_2$ denotes methyl;
R$_3$ denotes methyl, ethyl or methoxyethyl;
R$_6$ denotes hydrogen;
R$_7$ denotes hydrogen;
R$_8$ denotes hydrogen,
R$_9$ denotes hydrogen; and
A denotes ethylene or propylene;
or a salt thereof.

11. A compound selected from the group consisting of
3-methyl 5-[3-(4,4-diphenylpiperid-1-yl)-propyl] 1,4-dihydro-2,6-dimethyl-4-(3-nitrophenyl)-pyridine-3,5-dicarboxylate,
3-methyl 5-[2-(4,4-diphenylpiperid-1-yl)-ethyl] 1,4-dihydro-2,6-dimethyl-4-(3-nitrophenyl)-pyridine-3,5-dicarboxylate,
3-methyl 5-[3-(4,4-diphenylpiperid-1-yl)-propyl] 4-(3-cyanophenyl)-1,4-dihydro-2,6-dimethylpyridine-3,5-dicarboxylate,
3-methyl 5-[2-(4,4-diphenylpiperid-1-yl)-2-methyl-propyl] 1,4-dihydro-2,6-dimethyl-4-(3-nitrophenyl)-pyridine-3,5-dicarboxylate,
3-ethyl 5-[3-(4,4-diphenylpiperid-1-yl)-propyl] 1,4-dihydro-2,6-dimethyl-4-(3-nitrophenyl)-pyridine-3,5-dicarboxylate,
3-methyl 5-[3-(4,4-diphenylpiperid-1-yl)-propyl] 1,4-dihydro-2,6-dimethyl-4-[3-(1,1,2,2-tetrafluoroethoxy)-phenyl]-pyridine-3,5-dicarboxylate,
3-methyl 5-[2-(4,4-diphenylpiperid-1-yl)-ethyl] 1,4-dihydro-2,6-dimethyl-4-[3-(1,1,2,2-tetrafluoroethoxy)-phenyl]-pyridine-3,5-dicarboxylate,
3-(2-methoxyethyl) 5-[2-(4,4-diphenylpiperid-1-yl)-ethyl] 1,4-dihydro-2,6-dimethyl-4-(3-nitrophenyl)-pyridine-3,5-dicarboxylate,
3-(2-methoxyethyl) 5-[3-(4,4-diphenylpiperid-1-yl)-propyl] 1,4-dihydro-2,6-dimethyl-4-(3-nitrophenyl)-pyridine-3,5-dicarboxylate,
3-methyl 5-{3-[4,4-di(4-methoxyphenyl)-piperid-1-yl]propyl} 1,4-dihydro-2,6-dimethyl-4-(3-nitrophenyl)-pyridine-3,5-dicarboxylate,
3-methyl 5-[4-(4,4-diphenylpiperid-1-yl)-butyl] 1,4-dihydro-2,6-dimethyl-4-(3-nitrophenyl)-pyridine-3,5-dicarboxylate,
3-methyl 5-[1,1-dimethyl-2-(4,4-diphenylpiperid-1-yl)-ethyl] 1,4-dihydro-2,6-dimethyl-4-(3-nitrophenyl)-pyridine-3,5-dicarboxylate,
3-ethyl 5-[3-(4,4-diphenylpiperid-1-yl)-propyl] 1,4-dihydro-2,6-dimethyl-4-(2-difluoromethoxyphenyl)-pyridine-3,5-dicarboxylate,
1,4-dihydro-2,6-dimethyl-4-(3-nitrophenyl)-pyridine-3,5-dicarboxylic acid 3-[3-(4,4-diphenylpiperid-1-yl)-propyl ester],
3-ethyl 5-[3-(4,4-diphenylpiperid-1-yl)-propyl] 1,4-dihydro-2,6-dimethyl-4-[3-(1,1,2,2-tetrafluoroethoxy)-phenyl]-pyridine-3,5-dicarboxylate,
3-ethyl 5-[3-(4,4-diphenylpiperid-1-yl)-propyl] 1,4-dihydro-2,6-dimethyl-4-(3-difluoromethoxyphenyl)-pyridine-3,5-dicarboxylate,
3-methyl 5-[3-(4,4-diphenylpiperid-1-yl)-propyl] 4-(2,3-dichlorophenyl)-1,4-dihydro-2,6-dimethylpyridine-3,5-dicarboxylate,
3-methyl 5-[3-(4,4-diphenylpiperid-1-yl)-propyl] 4-(2,1,3-benzoxadiazol-4-yl)-1,4-dihydro-2,6-dimethylpyridine-3,5-dicarboxylate,
3-methyl 5-[3-(4,4-diphenylpiperid-1-yl)-propyl] 1,4-dihydro-2,6-dimethyl-4-(3-fluorophenyl)-pyridine-3,5-dicarboxylate,
3-methyl 5-[3-(4,4-diphenylpiperid-1-yl)-propyl] 1,4-dihydro-2,6-dimethyl-4-(2-trifluoromethylphenyl)-pyridine-3,5-dicarboxylate,
3-ethyl 5-[3-(4,4-diphenylpiperid-1-yl)-propyl] 4-(2-cyanophenyl)-1,4-dihydro-2,6-dimethylpyridine-3,5-dicarboxylate, 3-methyl 5-[3-(4,4-diphenylpiperid-1-yl)-propyl] 4-(2-chlorophenyl)-1,4-dihydro-2,6-dimethylpyridine-3,5-dicarboxylate hydrochloride,
and a salt of one of the previously-enumerated compounds.

12. The compound of claim 1 which is 3-methyl 5-[3-(4,4-diphenylpiperid-1-yl)-propyl] 1,4-dihydro-2,6-dimethyl-4-(3-nitrophenyl)-pyridine-3,5-dicarboxylate or a salt thereof.

13. A compound according to claim 1, wherein Y denotes

or a salt thereof.

14. A compound according to claim 1, wherein Y denotes

or a salt thereof.

15. A medicament composition comprising from 0.1 to 95 percent by weight of active ingredient in addition to a suitable pharmaceutical auxiliary and wherein the active ingredient comprises one or more compounds according to claim 1 or pharmacologically-acceptable salt thereof.

16. A composition according to claim 15 in unit dosage form.

17. A medicament composition for treatment or prophylaxis of hypertension, coronary heart disease, disturbance in peripheral and cerebral circulation and/or disease based on an increased retention of water or sodium and which comprises an effective amount of a compound of formula I of claim 1 or a pharmacologically-acceptable salt thereof.

18. A treatment or prophylaxis of hypertension, coronary heart disease, disturbance in peripheral and cerebral circulation and/or disease based on an increase retention of water or sodium which comprises administering an effective amount of pharmaceutically-active compound to a mammal prone to or afflicted with one or more of these ailments, the improvement wherein the pharmaceutically-active compound is a compound of formula I according to claim 1 or a pharmacologically-acceptable salt thereof.

* * * * *